US008993959B2

(12) United States Patent
Goh et al.

(10) Patent No.: US 8,993,959 B2
(45) Date of Patent: Mar. 31, 2015

(54) SCREENING FOR PHTHALATES IN FOOD SAMPLES

(71) Applicant: Waters Technologies Corporation, Milford, MA (US)

(72) Inventors: Evelyn Mei Ling Goh, Singapore (SG); Melvin Choon Lin Gay, Singapore (SG)

(73) Assignee: Waters Technologies Corporation, Milford, MA (US)

( * ) Notice: Subject to any disclaimer, the term of this patent is extended or adjusted under 35 U.S.C. 154(b) by 0 days.

(21) Appl. No.: 14/358,433

(22) PCT Filed: Nov. 2, 2012

(86) PCT No.: PCT/US2012/063158
§ 371 (c)(1),
(2) Date: May 15, 2014

(87) PCT Pub. No.: WO2013/077985
PCT Pub. Date: May 30, 2013

(65) Prior Publication Data
US 2014/0319334 A1    Oct. 30, 2014

Related U.S. Application Data

(60) Provisional application No. 61/562,114, filed on Nov. 21, 2011.

(51) Int. Cl.
*G01N 30/72*    (2006.01)
*G01N 33/02*    (2006.01)
(52) U.S. Cl.
CPC ............... *G01N 30/72* (2013.01); *G01N 33/02* (2013.01)
USPC ........................................................ 250/288

(58) Field of Classification Search
USPC ........................................................ 250/288
See application file for complete search history.

(56) References Cited

U.S. PATENT DOCUMENTS

| 7,161,145 B2 | 1/2007 | Oser et al. |
| 8,211,715 B1 * | 7/2012 | Royds ........................... 422/403 |

FOREIGN PATENT DOCUMENTS

WO    2011017418 A1    2/2011

OTHER PUBLICATIONS

Goh et al. "Rapid Screening for Phthalates in Food and Beverages Using Atmosphere Solids Analysis Probe (ASAP) with Xevo TQ MS", Waters: the Science of What's Possible [Application Note]: pp. 1-6, Aug. 2011.
Shimadzu Scientifi C Instruments, "Advantages of LCMS-IT-TOF Mass Spectrometry in identiying Polymer Additives," pp. 1-9, Aug. 2009.
Cleland et al. "Ambient Thermal Desorption Ionization for Rapid Mass Spectrometric Analysis of Contaminants," Waters: the Science of What's Possible: Poster presentation, Aug. 16, 2011.
(Continued)

*Primary Examiner* — Kiet T Nguyen
(74) *Attorney, Agent, or Firm* — Waters Technologies Corporation

(57) ABSTRACT

A method includes the steps of dipping a capillary (e.g., a disposable glass capillary) into a food matrix to deposit a food sample on the capillary; attaching the capillary onto an Atmospheric Solids Analysis Probe (ASAP); loading the ASAP into an atmospheric pressure ionization (API) source enclosure; ionizing the food sample on the capillary within the API source enclosure; and analyzing the ionized sample for the presence of one or more phthalates.

15 Claims, 4 Drawing Sheets

(56) References Cited

OTHER PUBLICATIONS

Leitz et al. "Chemical Analysis and Risk Assessment of Diethyl Phthalate in Alcoholic Beverages with Special Regard to Unrecorded Alcohol" Plos ONE, Dec. 2, 2009, vol. 4, No. 12, pp. e8127. entire document.

International Search Report for PCT/US2012/063158, dated Jan. 18, 2013, 4 pages.

International Written Opinion Report for PCT/US2012/063158, dated Jan. 18, 2013, 4 pages.

McEwen et al; Analysis of Solids, Liquids, and Biological Tissues Using Solids Probe Introductioon at Atmospheric Pressure on Commercial LC/MS Instruments:, Anal. Chem. 2005, 77, 7826-7831.

Technical Note—Product Solution; "Waters Atmospheric Solids Analysis Probe Rapidly Delivers Direct Analysis Within Minutes", Waters Corporation, May 2010.

* cited by examiner

SCREENING FOR PHTHALATES IN FOOD SAMPLES

RELATED APPLICATIONS

This application is the National Stage of International Application No. PCT/US2012/063158, filed Nov. 2, 2012, which claims priority to and benefit of U.S. provisional application no. 61/562,114, filed Nov. 21, 2011, entitled "Screening for Phthalates in Food Samples." The contents and teachings of each of these applications are hereby expressly incorporated herein by reference in their entirety.

TECHNICAL FIELD

The invention relates generally to methods for screening for phthalates in food samples.

BACKGROUND

Phthalates (esthers of phthalic acid) are additives that are widely used in plastics and other materials, primarily to make them soft and flexible. They are used in industry as well as in medical and consumer products. Since phthalates are not chemically bound to plastics, they can be easily released into the environment. Thus, phthalates present in packaging materials may also be released into foods and beverages.

In June 2011, a notification was sent out by the U.S. Food and Drug Administration (FDA) to manufacturers of food products and suppliers of food ingredients regarding the potential adulteration of emulsifiers with undeclared phthalate plasticizers; specifically di-2-ethylhexyl phthalate (DEHP). In May 2011, the Taiwan Food and Drug Administration (TFDA) found DEHP in powdered probiotics, which was traced back to the clouding agent (emulsifier) supplier. This so-called clouding agent is a legal food additive that is commonly used in beverage, food, and dietary supplements. Clouding agents are generally made of acacia gum, emulsifier, palm oil, and various food additives. However, it is believed that the supplier intentionally replaced the additives with DEHP in order to maximize profits.

The FDA initiated a heightened surveillance program to screen suspect food products from Taiwan for DEHP and other plasticizers, such as butylbenzyl phthalate (BBP), di-n-butyl phthalate (DBP), di-n-octyl phthalate (DNOP), di-isononyl phthalate (DINP), and di-isodecyl phthalate (DIDP). Rigorous tests were carried out on various food and beverage products, including sport drinks, fruit juices, teas, fruit jams and jellies, food powders, and dietary supplement tablets. Known methods of screening for phthalates have been based on gas chromatography/mass spectrometry (GC/MS) and liquid chromatography/mass spectrometry (LC/MS).

SUMMARY

This disclosure is based, in part, on the realization that an Atmospheric Solids Analysis Probe (ASAP) can be a useful tool for the rapid direct analysis of phthalates in food matrices. Current phthalate analysis methods may require extensive sample preparation prior to analysis (depending on the food matrix), and this can slow down the data turnaround time. An advantage of using an ASAP is that it can be used to analyze complex samples without the need for extensive sample preparation or even chromatographic separation.

One aspect features a method that includes the steps of dipping a capillary (e.g., a disposable glass capillary) into a food matrix to deposit a food sample on the capillary; attaching the capillary onto an Atmospheric Solids Analysis Probe (ASAP); loading the ASAP into an atmospheric pressure ionization (API) source enclosure; ionizing the food sample on the capillary within the API source enclosure; and analyzing the ionized sample for the presence of one or more phthalates.

Implementations may include one or more of the following features.

In some implementations, after dipping and prior to loading the ASAP into API source enclosure, excess food sample is removed from the capillary (e.g., by wiping the capillary with a lint-free tissue).

In certain implementations, sample preparation is performed on the food matrix prior to dipping the capillary into the food matrix. Sample preparation can include, for example, grinding the food matrix into a powder.

In some implementations, the step of performing sample preparation through the completion of the analyzing step is all completed in less than 2 minutes.

The food matrix can be a solid food matrix, a powder food matrix, a liquid food matrix, or a gel-like food matrix.

In certain implementations, the step of dipping through the completion of the analyzing step is all completed in less than 2 minutes.

In some implementations, the analyzing step is completed in less than 1.5 minutes.

In certain implementations, the ionized sample is analyzed using a tandem quadrupole mass spectrometer.

In some implementations, the ionized sample is analyzed using a time-of-flight (TOF) mass spectrometer.

In certain implementations, analyzing the ionized sample includes acquiring mass spectrometric data confirming the presence or absence of one or more phthalates in the food matrix.

In some implementations, analyzing the ionized sample includes detecting the presence one or more phthalates in an amount of about 1 ppm to about 1.5 ppm.

In certain implementations, analyzing the ionized sample includes detecting the presence one or more phthalates in an amount less than 1.5 ppm.

In some cases, the one or more phthalates are selected from di-2-ethylhexyl phthalate (DEHP), butylbenzyl phthalate (BBP), di-n-butyl phthalate (DBP), di-n-octyl phthalate (DNOP), di-isononyl phthalate (DINP), and di-isodecyl phthalate (DIDP).

Implementations can provide one or more of the following advantages.

In some implementations, complex food samples can be screened for phthalates without the need for chromatographic separation.

In certain implementations, complex food samples can be screened for phthalates with minimal or no sample preparation.

In some implementations, the time required to screen a food sample for the presence of phthalates can take less than 2 minutes from sample preparation through analysis. This can help to increase sample throughput and lab efficiency. For example, this initial quick screening can allow food testing labs to reduce the number of samples that require testing, allowing for faster turnaround times.

In certain implementations, the use of different extraction techniques for complex food matrices may be eliminated.

In some implementations, the detection of phthalates at legislated control levels is provided.

In certain implementations, the chances of sample carryover can be reduced by using a new capillary for every sample. This can also help to minimize the number of false positives in the screening of the food samples.

Other aspects, features, and advantages are in the description, drawings, and claims.

BRIEF DESCRIPTION OF THE DRAWINGS

Like reference numbers indicate like elements.

DETAILED DESCRIPTION

In disclosed methods, an Atmospheric Solids Analysis Probe (ASAP) is used in combination with a mass spectrometer to rapidly screen for the presence of phthalates in food matrices. Current known methods of analyzing phthalates are commonly based on gas chromatography/mass spectrometry (GC/MS) and liquid chromatography/mass spectrometry (LC/MS). Due to the complexity of food matrices, the use of different extraction techniques is often required. With the disclosed methods, sample preparation is minimal and no chromatographic separation is required.

Figure 1:
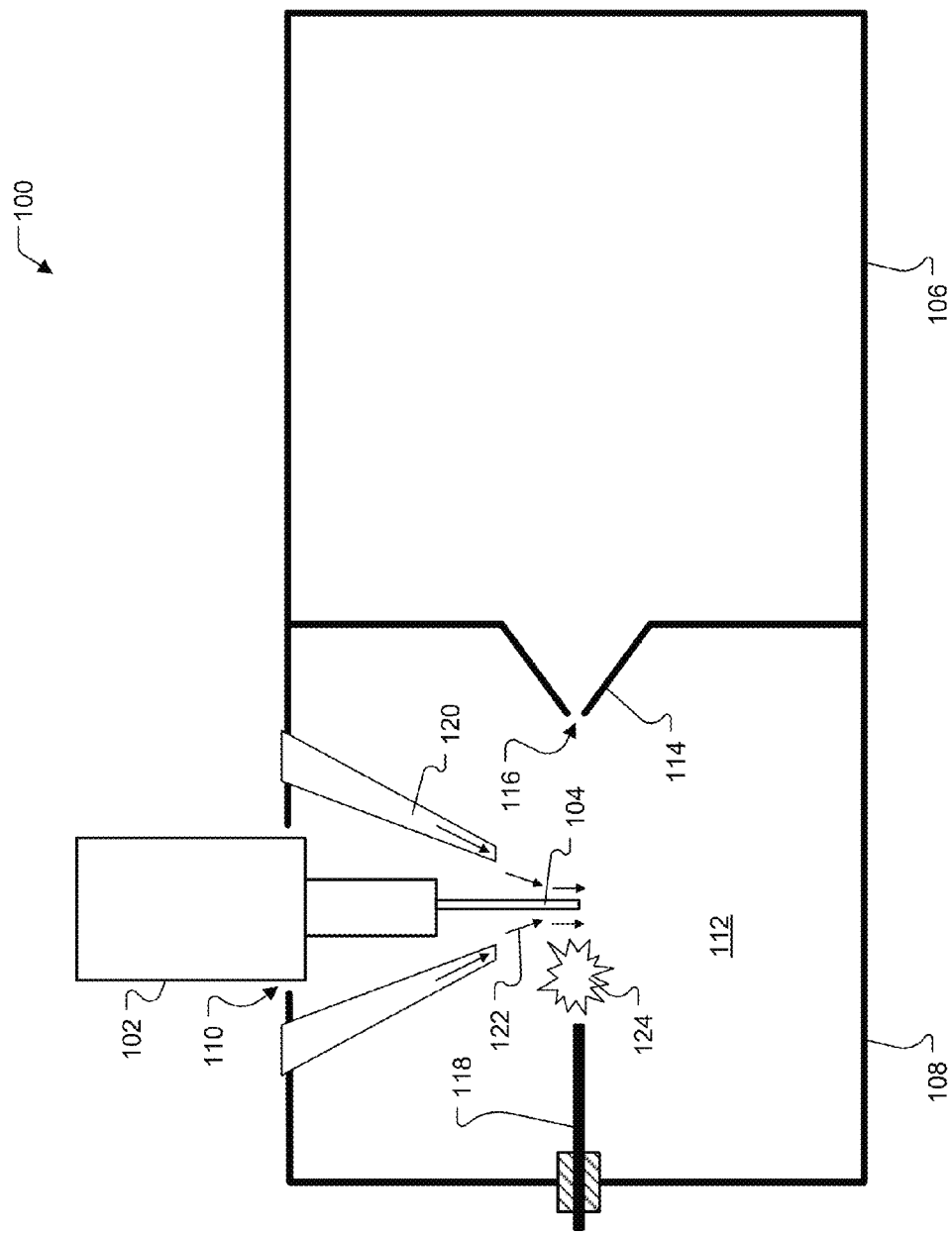
FIG. 1 is a schematic view of an apparatus for screening for phthalates in food samples.

FIG. 1 illustrates an exemplary apparatus 100 that can be employed for performing direct analysis of food samples. The apparatus 100 includes an Atmospheric Solids Analysis Probe (ASAP) 102, a disposable glass capillary 104, a mass spectrometer 106, and an atmospheric pressure ionization (API) source enclosure 108. The ASAP 102 receives the capillary 104 and is inserted into an aperture 110 of the source enclosure 108 such that a distal end of the capillary 104 extends into an inner volume 112 of the source enclosure 108. A suitable ASAP 102 is commercially available from Waters Corporation, Milford, Mass., USA.

The mass spectrometer 106 includes an extractor cone 114 having an ion receiving orifice 116. The extractor cone 114 interfaces with the inner volume 112 of the source enclosure 108, for receiving ions therefrom. Suitable mass spectrometers include tandem quadrupole mass spectrometers and time-of-flight (TOF) mass spectrometers. Mass spectrometers of these types are available from Waters Corporation.

The source enclosure 108 houses an electrode (corona pin 118) and a jet element 120. The jet element 120 is configured to direct a flow of heated desolvation gas (e.g., nitrogen, helium, argon, or neon), as illustrated by arrows 122, towards a sample retained on the outer surface of the glass capillary 104 to volatilize the sample. The volatilized sample is then ionized by a corona discharge 124 provided by the corona discharge pin 118. The ions flow into the mass spectrometer 106 through the inlet 116 of the extractor cone 114 by the combined effects of electrostatic attraction and vacuum.

Figure 2:
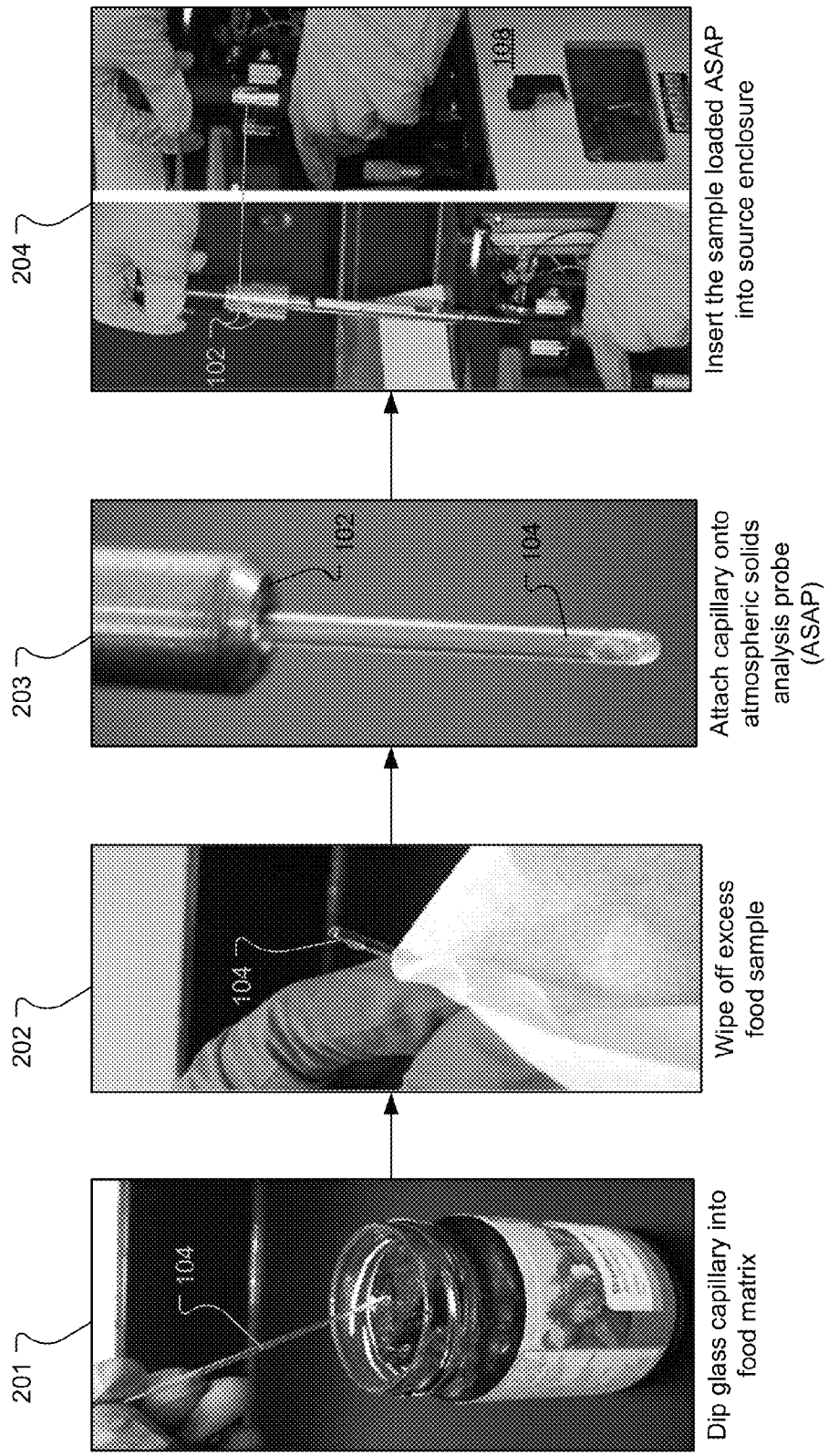
FIG. 2 is a flow diagram of an example process for screening for phthalates in a food sample.

Referring to FIG. 2, for the detection of phthalates in food, the glass capillary 104 is dipped into a food matrix (201) to deposit a food sample on the surface of the glass capillary 104, and excess sample is wiped off with a lint-free tissue (202) leaving behind a residue. The sample may have any one of a variety matrix types including solid (e.g., health supplement tablets, biscuits), powder (e.g., milk powder, grounded spices) liquid (e.g., syrup, fruit juice, milk), and gel-like (e.g., jams, creams). The process may vary slightly depending on the matrix type. For example, additional sample preparation may be required for solid matrices, which may need to be ground into powder before the glass capillary 104 is dipped into the sample. Once the excess sample has been wiped off, the glass capillary 104 is attached onto the ASAP (203) and the ASAP 102 is then loaded into the source enclosure 108 for analysis (204).

During the analysis, a current of about 10 µA is applied to the corona pin 118; the desolvation gas ($N_2$) is heated to a temperature of about 400° C. to about 500° C., e.g., 450° C. and delivered into the source enclosure 108 at a flow rate of about 800 L/min; the ion source is maintained at a temperature of about 150° C.; and multiple reaction monitoring (MRM) data is acquired, using the MRM parameters specified in Table 1 (below), over an acquisition time range of 0.3 to 1.5 minutes. Ionization was performed in ASAP positive mode.

TABLE 1

| Analyte | Precursor Ion | Product Ion | Cone Voltage (V) | Collision Energy (eV) |
|---|---|---|---|---|
| BBP | 313.14 | 149 | 17 | 11 |
|  |  | 205 |  | 7 |
|  |  | 239 |  | 5 |
| DBP | 279.16 | 149 | 20 | 14 |
|  |  | 205 |  | 17 |
| *DEHP | 391.28 | 149 | 19 | 20 |
|  |  | 167 |  | 14 |
|  |  | 279 |  | 9 |
| *DNOP | 391.28 | 149 | 18 | 12 |
|  |  | 261 |  | 10 |
|  |  | 121 |  | 40 |
| DINP | 419.31 | 149 | 15 | 26 |
|  |  | 275 |  | 12 |
|  |  | 293 |  | 13 |
| DIDP | 447.35 | 149 | 18 | 25 |
|  |  | 289 |  | 9 |
|  |  | 307 |  | 11 |

*DEHP and DNOP are isomers.

EXAMPLE

The list of six prohibited phthalates (DEHP, BBP, DBP, DNOP, DINP, and DIDP) was rapidly screened in food samples using the above described method and a Xevo™ TQ MS mass spectrometer, available from Waters Corporation, equipped with a Waters Atmospheric Solids Analysis Probe (ASAP). In this experiment, four food matrices were screened for the presence of phthalates: flavored syrup, fruit juice, jam, and dietary supplement tablets. In all cases, minimal sample preparation was required and no chromatographic separation was used for the analysis.

Figure 3:
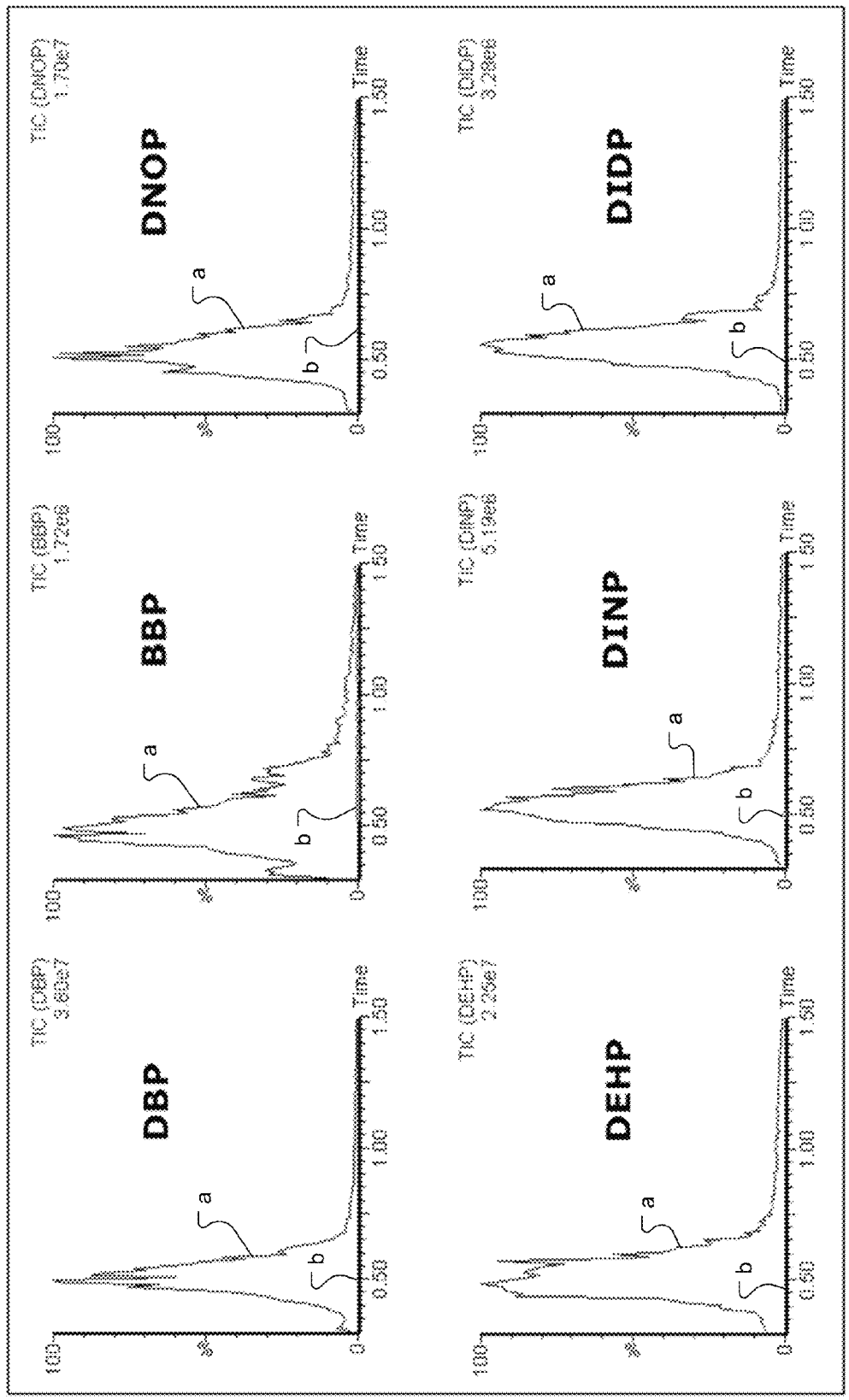
FIG. 3 shows total ion current (TIC) traces of six phthalates detected in fruit juice in comparison with a matrix blank.

FIG. 3 shows the total ion current (TIC) traces of the six phthalates analyzed, spiked at 1 ppm (trace 'a') in comparison with the matrix blank (trace 'b') in fruit juice. The phthalates were successfully detected at 1 ppm, which is below the levels stipulated by the Food Containers and Appliances (Taiwan). The MS analysis was completed in less than 1.5 minutes, and the total time from sample preparation to analysis was achieved in less than 2 minutes.

Figure 4:
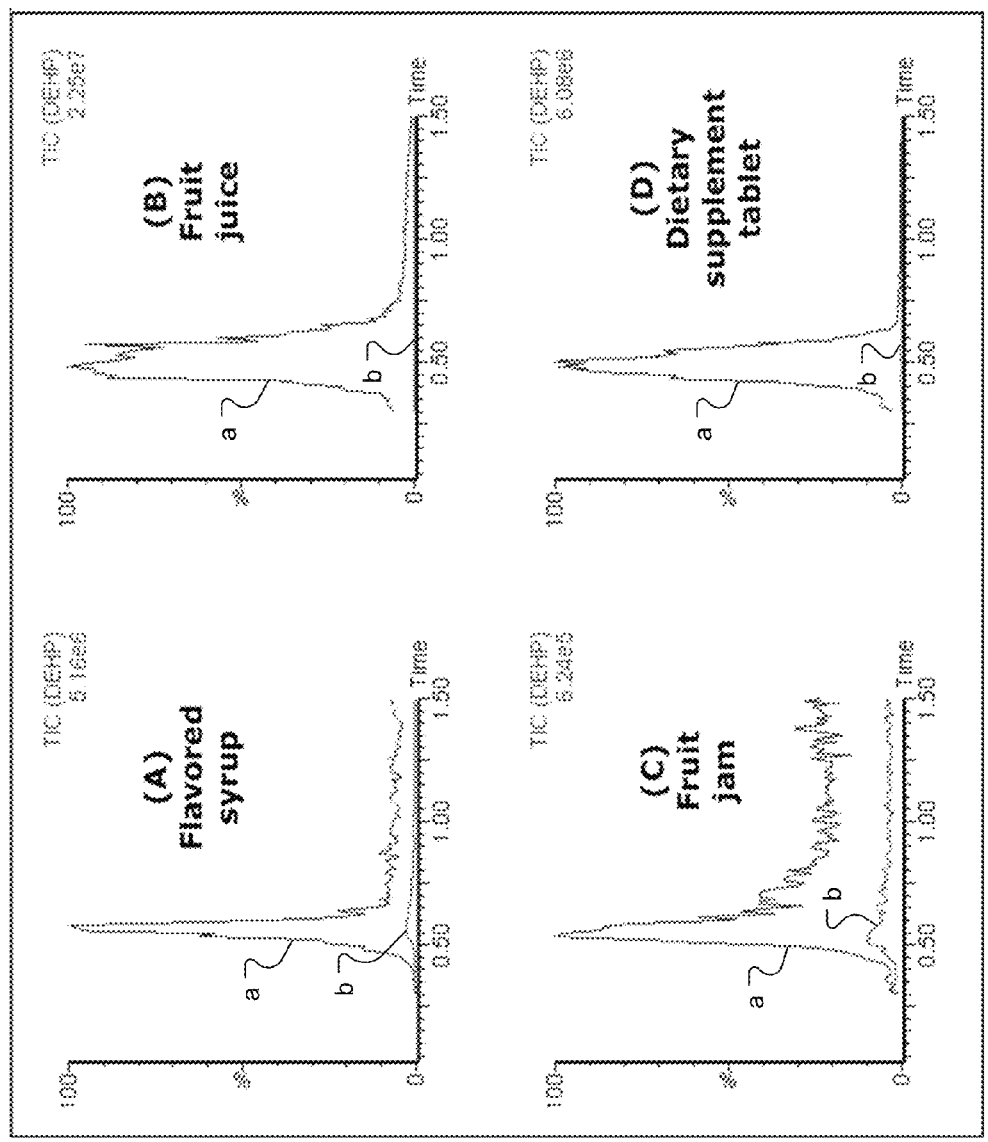
FIG. 4 shows the results of detection of di-2-ethylhexyl phthalate (DEHP) in various food matrices.

Of particular interest among the six phthalates is DEHP, which was the plasticizer contaminant that was first found in the clouding agents in Taiwan. The results of DEHP in various food matrices using ASAP and a Xevo™ TQ mass spectrometer are illustrated in FIG. 4. FIG. 4 shows TIC traces of DEHP spikes at 1 mg/kg (trace 'a') in comparison with a matrix blank (trace 'b') in flavored syrup (A), fruit juice (B), fruit jam (C), and dietary supplement tablets (D). The results demonstrate the potential of using ASAP for quick screening of DEHP and other prohibited phthalates in food regulatory and contract testing labs that require fast turnaround analysis times.

Although a few implementations have been described in detail above, other modifications are possible. Accordingly, other implementations are within the scope of the following claims.

What is claimed is:

1. A method comprising:
   dipping a capillary into a food matrix to deposit a food sample on the capillary;
   attaching the capillary onto an Atmospheric Solids Analysis Probe (ASAP);
   loading the ASAP into an atmospheric pressure ionization (API) source enclosure;
   ionizing the food sample on the capillary within the API source enclosure; and
   analyzing the ionized sample for the presence of one or more phthalates.

2. The method of claim 1, further comprising, after dipping and prior to loading the ASAP into API source enclosure, removing excess food sample from the capillary.

3. The method of claim 1, wherein the capillary is a disposable glass capillary.

4. The method of claim 1, further comprising performing sample preparation on the food matrix prior to dipping the capillary into the food matrix.

5. The method of claim 4, wherein performing sample preparation comprises grinding the food matrix into a powder.

6. The method of claim 4, wherein the step of performing sample preparation through the completion of the analyzing step are completed in less than 2 minutes.

7. The method of claim 1, wherein the food matrix is a solid food matrix, a powder food matrix, a liquid food matrix, or a gel-like food matrix.

8. The method of claim 1, wherein the steps of dipping through the completion of the analyzing step are completed in less than 2 minutes.

9. The method of claim 1, wherein the analyzing step is completed in less than 1.5 minutes.

10. The method of claim 1, wherein the ionized sample is analyzed using a tandem quadrupole mass spectrometer.

11. The method of claim 1, wherein the ionized sample is analyzed using a time-of-flight (TOF) mass spectrometer.

12. The method of claim 1, wherein analyzing the ionized sample comprises acquiring mass spectrometric data confirming the presence or absence of one or more phthalates in the food matrix.

13. The method of claim 1, wherein analyzing the ionized sample comprises detecting the presence one or more phthalates in an amount of about 1 ppm to about 1.5 ppm.

14. The method of claim 1, wherein analyzing the ionized sample comprises detecting the presence one or more phthalates in an amount less than 1.5 ppm.

15. The method of claim 1, wherein the one or more phthalates are selected from the group consisting of di-2-ethylhexyl phthalate (DEHP), butylbenzyl phthalate (BBP), di-n-butyl phthalate (DBP), di-n-octyl phthalate (DNOP), di-isononyl phthalate (DINP), and di-isodecyl phthalate (DIDP).

* * * * *